(12) United States Patent
Kim et al.

(10) Patent No.: US 12,274,774 B2
(45) Date of Patent: Apr. 15, 2025

(54) COSMETIC COMPOSITION DERIVED FROM NATURAL PRODUCTS FOR IMPROVING SKIN HEALTH

(71) Applicant: SEOUL NATIONAL UNIVERSITY R&DB FOUNDATION, Seoul (KR)

(72) Inventors: Seong Keun Kim, Suwon-si (KR); Eun Hak Lim, Seoul (KR); Kyoung Chan Park, Incheon (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 18/399,796

(22) Filed: Dec. 29, 2023

(65) Prior Publication Data

US 2024/0148624 A1 May 9, 2024

Related U.S. Application Data

(63) Continuation of application No. PCT/KR2021/014124, filed on Oct. 13, 2021.

(30) Foreign Application Priority Data

Jul. 2, 2021 (KR) .................. 10-2021-0087367
Sep. 14, 2021 (KR) .................. 10-2021-0122608

(51) Int. Cl.
| | | |
|---|---|---|
| *A61K 8/35* | (2006.01) | |
| *A61K 8/02* | (2006.01) | |
| *A61Q 17/00* | (2006.01) | |
| *A61Q 17/04* | (2006.01) | |
| *A61Q 19/02* | (2006.01) | |
| *A61Q 19/08* | (2006.01) | |

(52) U.S. Cl.
CPC .............. *A61K 8/35* (2013.01); *A61K 8/0216* (2013.01); *A61Q 17/005* (2013.01); *A61Q 17/04* (2013.01); *A61Q 19/02* (2013.01); *A61Q 19/08* (2013.01); *A61K 2800/522* (2013.01)

(58) Field of Classification Search
None
See application file for complete search history.

(56) References Cited

U.S. PATENT DOCUMENTS

| | | |
|---|---|---|
| 10,787,607 B2 | 9/2020 | Kim |
| 2003/0118617 A1 | 6/2003 | Soby |
| 2015/0031867 A1* | 1/2015 | Kim .................. H10K 50/11 560/138 |
| 2017/0151168 A1* | 6/2017 | Constantine ............. A61K 8/35 |
| 2021/0177992 A1 | 6/2021 | Kim |

FOREIGN PATENT DOCUMENTS

| | | |
|---|---|---|
| KR | 10-1997-0020091 A | 5/1997 |
| KR | 10-1002432 B1 | 12/2010 |
| KR | 10-1244176 B1 | 3/2013 |
| KR | 10-1294993 B1 | 8/2013 |
| KR | 10-1480600 B1 | 1/2015 |
| KR | 10-2018-0003920 A | 1/2018 |
| KR | 10-2018-0061664 A | 6/2018 |
| KR | 10-2019-0069317 A | 6/2019 |
| WO | 2010014361 A1 | 2/2010 |

OTHER PUBLICATIONS

International Search Report of PCT/KR2021/014124 dated Mar. 29, 2022.
Ilseung Yang et al., Photochemical generation of a new, highly fluorescent compound from non-fluorescent resveratrol, Chemical Communication, 2012, vol. 48, No. 31, pp. 3839-3841.
T. Rodríguez-Cabo et al., Comprehensive evaluation of the phototransformation routes of trans-resveratrol, Journal of Chromatography A, 2015, vol. 1410, pp. 129-139.
Korean Intellectual Property Office Notice of Preliminary Rejection and its English translation.
Korean Intellectual Property Office Notice of Allowance and its English translation.
Extended European Search Report for Application No. 21948556.2, dated Jan. 31, 2025.

\* cited by examiner

*Primary Examiner* — Nannette Holloman
(74) *Attorney, Agent, or Firm* — Shih IP Law Group, PLLC.

(57) ABSTRACT

The present application relates to a cosmetic composition comprising resveratrone, for improving skin health.

4 Claims, 9 Drawing Sheets

SPF measurement

PFA measurement

COSMETIC COMPOSITION DERIVED FROM NATURAL PRODUCTS FOR IMPROVING SKIN HEALTH

CROSS-REFERENCE TO RELATED APPLICATIONS

This application is a continuation of PCT Application No. PCT/KR2021/014124, filed on Oct. 13, 2021, which claims priorities to Korean Patent Applications No. 10-2021-0087367 filed on Jul. 2, 2021, and No. 10-2021-0122608 filed on Sep. 14, 2021, all of which are hereby incorporated by reference in their entirety.

TECHNICAL FIELD

The present disclosure relates to a cosmetic composition including resveratrone for improving skin health.

BACKGROUND

Resveratrone is a compound derived from a natural product, resveratrol, and the structure of the compound and preparation methods of the compound have been patented [Korean Patent No. 1294993, U.S. Pat. No. 10,787,607]. Also, anticancer effects of resveratrone have been reported [Korean Patent No. 2169585], but the efficacy related to skin health has not been known so far.

DISCLOSURE OF THE INVENTION

Problems to be Solved by the Invention

The present disclosure is conceived to provide a cosmetic composition including resveratrone for improving skin health.

However, problems to be solved by the present disclosure are not limited to the above-described problems. Although not described herein, other problems to be solved by the present disclosure can be clearly understood by those skilled in the art from the following descriptions.

Means for Solving the Problems

A first aspect of the present disclosure provides a cosmetic composition including a compound represented by Chemical Formula 1 as an active ingredient:

[Chemical Formula 1]

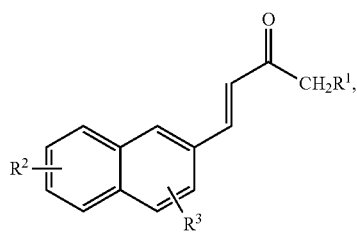

in Chemical Formula 1, $R^1$ is hydrogen; a halogen group; a linear or branched $C_{1-6}$ alkyl group; a $C_{3-6}$ cycloalkyl group; a linear or branched $C_{1-6}$ alkoxy group; a $C_{2-6}$ heterocycloalkyl group containing N, O, or S as a hetero atom; or a phenyl group unsubstituted or substituted with one or more substituents selected from a halogen group, amino group, nitrile group, nitro group, a $C_{1-10}$ alkyl group, a $C_{2-10}$ alkenyl group, a $C_{1-10}$ alkoxy group, a $C_{3-6}$ cycloalkyl group, a $C_{2-6}$ heterocycloalkyl group containing N, O, or S as a hetero atom, a $C_{6-16}$ aryl group, and a $C_{5-15}$ heteroaryl group containing N, O, or S as a hetero atom, and Each of $R^2$ and $R^3$ is independently selected from hydroxyl group, a linear or branched $C_{1-6}$ alkoxy group, and a benzoyl group.

A second aspect of the present disclosure provides a monofunctional or multifunctional cosmetic including the cosmetic composition according to the first aspect.

Effects of the Invention

A cosmetic composition including a resveratrone compound according to embodiments of the present disclosure has a skin regeneration effect by inducing cell proliferation, an antioxidant effect by removing active oxygen, and a skin whitening effect by inhibiting melanin synthesis and activities of tyrosinase.

The cosmetic composition including a resveratrone compound according to embodiments of the present disclosure has skin elasticity enhancement and wrinkle improvement effects by promoting collagen synthesis, an antibacterial (anti-acne) effect on the skin by inhibiting the growth of acne-causing bacteria, and a sun protection effect.

BEST MODE FOR CARRYING OUT THE INVENTION

Figure 1:
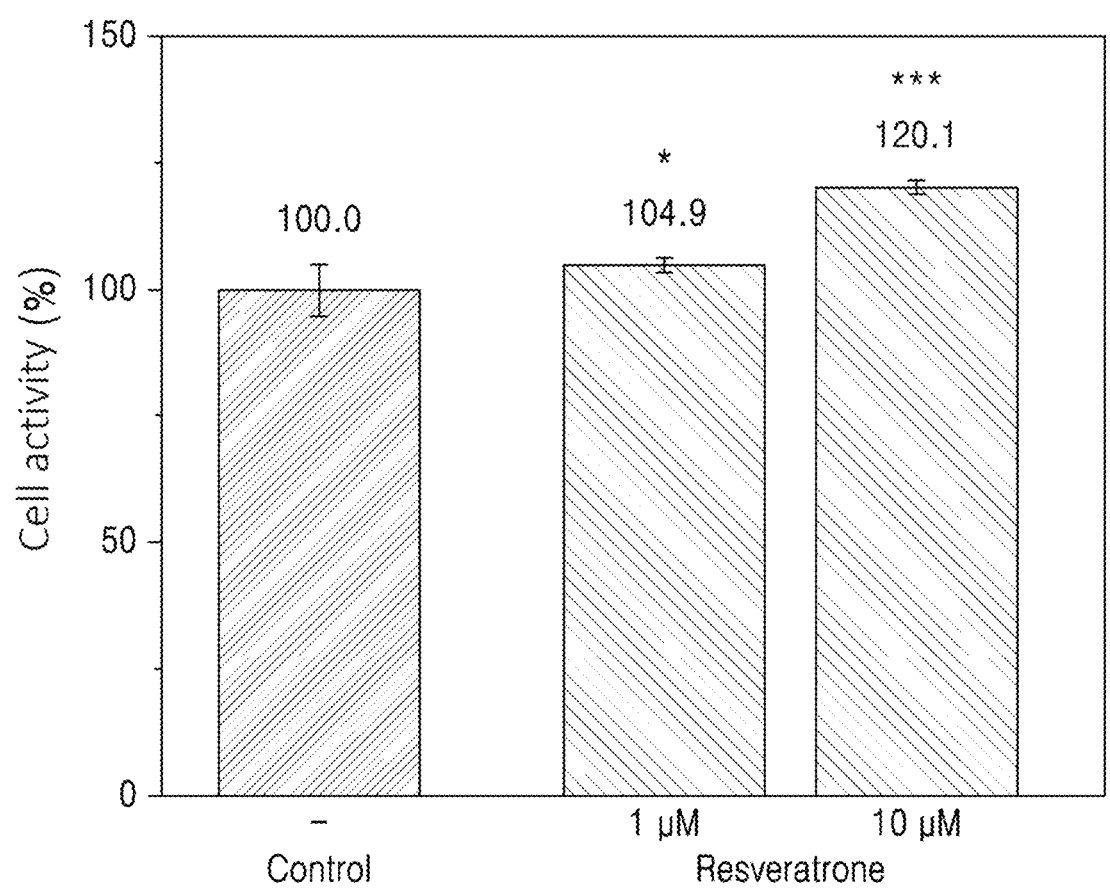
FIG. 1 is a graph showing the result of evaluating the cell proliferation efficacy of resveratrone compounds according to an example of the present disclosure.

Hereinafter, embodiments and examples of the present disclosure will be described in detail with reference to the accompanying drawings so that the present disclosure may be readily implemented by those skilled in the art. However, it is to be noted that the present disclosure is not limited to the examples but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element.

Through the whole document, the term "on" that is used to designate a position of one element with respect to another element includes both a case that the one element is adjacent to the other element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party.

Through the whole document, the term "step of" does not mean "step for".

Through the whole document, the term "combination of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, a phrase in the form "A and/or B" means "A or B, or A and B".

Hereinafter, the present disclosure will be described in more detail with reference to exemplary embodiments. However, the present disclosure is not limited to these exemplary embodiments.

A first aspect of the present disclosure provides a cosmetic composition including a compound represented by Chemical Formula 1 as an active ingredient:

[Chemical Formula 1]

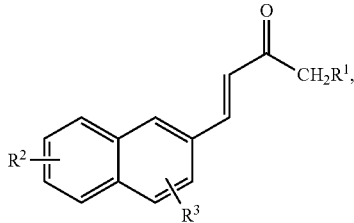

in Chemical Formula 1,
R$^1$ is hydrogen; a halogen group; a linear or branched C$_{1-6}$ alkyl group; a C$_{3-6}$ cycloalkyl group; a linear or branched C$_{1-6}$ alkoxy group; a C$_{2-6}$ heterocycloalkyl group containing N, O, or S as a hetero atom; or a phenyl group unsubstituted or substituted with one or more substituents selected from a halogen group, amino group, nitrile group, nitro group, a C$_{1-10}$ alkyl group, a C$_{2-10}$ alkenyl group, a C$_{1-10}$ alkoxy group, a C$_{3-6}$ cycloalkyl group, a C$_{2-6}$ heterocycloalkyl group containing N, O, or S as a hetero atom, a C$_{6-16}$ aryl group, and a C$_{5-15}$ heteroaryl group containing N, O, or S as a hetero atom, and Each of R$^2$ and R$^3$ is independently selected from hydroxyl group, a linear or branched C$_{1-6}$ alkoxy group, and a benzoyl group.

In an embodiment of the present disclosure, the compound represented by Chemical Formula 1 may be represented by the following Chemical Formula 2:

[Chemical Formula 2]

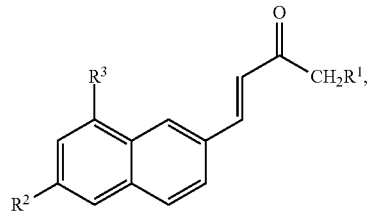

in Chemical Formula 2,
R$^1$ is hydrogen; a halogen group; a linear or branched C$_{1-6}$ alkyl group; a C$_{3-6}$ cycloalkyl group; a linear or branched C$_{1-6}$ alkoxy group; a C$_{2-6}$ heterocycloalkyl group containing N, O, or S as a hetero atom; or a phenyl group unsubstituted or substituted with one or more substituents selected from a halogen group, amino group, nitrile group, nitro group, a C$_{1-10}$ alkyl group, a C$_{2-10}$ alkenyl group, a C$_{1-10}$ alkoxy group, a C$_{3-6}$ cycloalkyl group, a C$_{2-6}$ heterocycloalkyl group containing N, O, or S as a hetero atom, a C$_{6-16}$ aryl group, and a C$_{5-15}$ heteroaryl group containing N, O, or S as a hetero atom, and Each of R$^2$ and R$^3$ is independently selected from hydroxyl group, a linear or branched C$_{1-6}$ alkoxy group, and a benzoyl group.

In an embodiment of the present disclosure, the compound represented by Chemical Formula 1 may be selected from

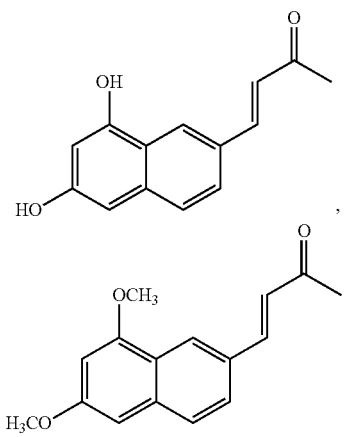

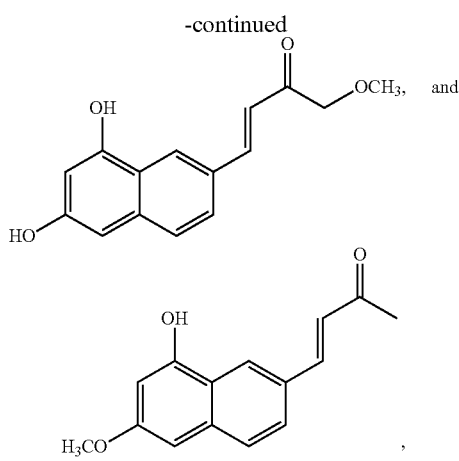

but may not be limited thereto.

In an embodiment of the present disclosure, the compound represented by Formula 1 may be a cosmetically acceptable salt. In an embodiment of the present disclosure, the salt may be an acid addition salt formed using an inorganic acid or an organic acid, and the inorganic acid includes one or more selected from hydrochloric acid, phosphoric acid, hydrobromic acid, nitric acid, carbonic acid, tartaric acid, boric acid, and carbonic acid, and the organic acid includes one or more selected from formic acid, acetic acid, lactic acid, butyric acid, citric acid, propionic acid, isobutyric acid, trifluoroacetic acid, malic acid, maleic acid, malonic acid, fumaric acid, succinic acid, succinic acid monoamide, glutamic acid, dichloroacetic acid, aminooxyacetic acid, tartaric acid, oxalic acid, citric acid, glycolic acid, glucuronic acid, galacturonic acid, ascorbic acid, benzoic acid, phthalic acid, salicylic acid, anthranilic acid, benzenesulfonic acid, p-toluenesulfonic acid, or methanesulfonic acid, but may not be limited thereto. In an embodiment of the present disclosure, the acid addition salt may be prepared by a general salt preparation method by which the compound represented by Chemical Formula 1 and an acid are mixed directly or mixed in the presence of a solvent.

A second aspect of the present disclosure provides a monofunctional or multifunctional cosmetic including the cosmetic composition according to the first aspect.

In an embodiment of the present disclosure, the multifunctionality may include one or more selected from skin regeneration, skin whitening, skin wrinkle improvement, anti-acne, sun protection, and antioxidation.

In an embodiment of the present disclosure, the skin regeneration means that skin tissue damaged by inflammation and wound is recovered by regeneration of skin cells, and the cosmetic for skin regeneration may have the effect of rapidly regenerating skin cells since the compound represented by Chemical Formula 1 helps cell proliferation.

In an embodiment of the present disclosure, the skin whitening means to brighten the color of the skin and improve skin pigmentation such as melasma and freckles, and the cosmetic for skin whitening may have the skin whitening effect since the compound represented by Chemical Formula 1 inhibits the synthesis of melanin pigment and inhibit the activity of melanin synthase.

In an embodiment of the present disclosure, the skin wrinkle improvement means to improve skin wrinkles or inhibit wrinkle formation by enhancing skin elasticity, and the cosmetic for skin wrinkle improvement may have the skin wrinkle improvement effect since the compound represented by Chemical Formula 1 helps the synthesis of collagen in the skin and thus enhances the elasticity of the skin.

In an embodiment of the present disclosure, the anti-acne (antibacterial) means to suppress or inhibit the growth of bacteria on the skin, and the antibacterial function may be implemented by the compound represented by Chemical Formula 1 that inhibits the growth of bacteria causing acne on the skin.

In an embodiment of the present disclosure, the antioxidant effect may be implemented by the compound represented by Chemical Formula 1 that removes active oxygen in the skin.

In an embodiment of the present disclosure, the cosmetic may include the cosmetic composition and thus may have skin regeneration, skin whitening, wrinkle improvement, antibacterial, skin antioxidant, and sun protection effects at the same time. The degree of each function may vary depending on the amount of the compound represented by Chemical Formula 1 and various products can be made by varying the amount thereof according to the purpose. In an embodiment of the present disclosure, the cosmetic may be a skin regeneration, skin whitening, skin wrinkle improvement, antibacterial (anti-acne), skin antioxidant and sun protection cosmetic.

In an embodiment of the present disclosure, a formulation of the cosmetic may be selected from toner, essence, lotion, cream, gel, powder, pack, surfactant of soap or shampoo, rinse, oil, foundation, hair dye, and wax, but may not be limited thereto. In an embodiment of the present disclosure, the cosmetic may further include a cosmetically acceptable adjuvant selected from surfactants, water, emulsifiers, fillers, fragrances, stabilizers, solubilizers, gellants, fatty substances, alcohols, and thickeners, but may not be limited thereto.

In an embodiment of the present disclosure, the formulation of the cosmetic may be an external preparation for skin selected from ointment, gel, cream, aerosol, and patch, but may not be limited thereto.

Hereinafter, example embodiments are described in more detail by using Examples, but the present disclosure may not limited to the Examples.

MODE FOR CARRYING OUT THE INVENTION

Examples

Example 1: Synthesis of Resveratrone

Resveratrone represented by Chemical Formula 3 was synthesized by the following method with reference to a prior art document [Korean Patent No. 1294993].

1) Resveratrol was dissolved in methanol at a concentration of 0.1 g/L to 1.0 g/L.
2) A special UV reactor equipped with a UV-B lamp ($\lambda_{max}$=306 nm) was used to irradiate a resveratrone solution with ultraviolet light.
3) After the reaction, the solution was concentrated and resveratrone was separated by using Prep-HPLC.

[Chemical Formula 3]

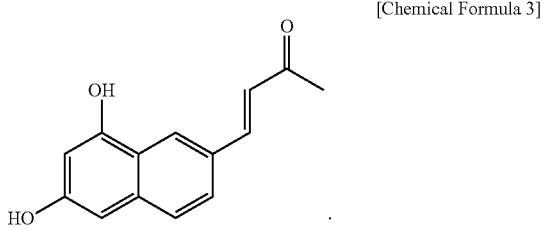 [SMILES: CC(=O)/C=C/c1ccc2cc(O)cc(O)c2c1]

Test Example 1: Evaluation of Cell Proliferation Efficacy of Resveratrone

1) Human-derived normal fibroblasts were cultured.
2) The cells were inoculated in an appropriate number, and after 24 hours, starvation was performed for 24 hours.
3) The cells were cultured for 72 hours in media treated with samples at different concentrations, respectively.
4) Cell activity was measured and analyzed by the MTT method.

Referring to FIG. 1, the cell proliferation efficacy was confirmed by an increase of 20% in number of cells in a test group treated with resveratrone at a concentration of 10 µM.

Test Example 2: Evaluation of Antioxidant Efficacy of Resveratrone (DPPH Assay)

1) 115 µL of 70% ethanol was dispensed to each of 96 wells.
2) 5 µL of each sample and positive control was dispensed, and the absorbance was measured at 517 nm to measure the absorbance before the reaction.
3) 80 µL of a DPPH solution was dispensed.
4) After the reaction, the absorbance was measured at 517 nm, and the result was analyzed by using the absorbance values before and after the reaction.

Figure 2:
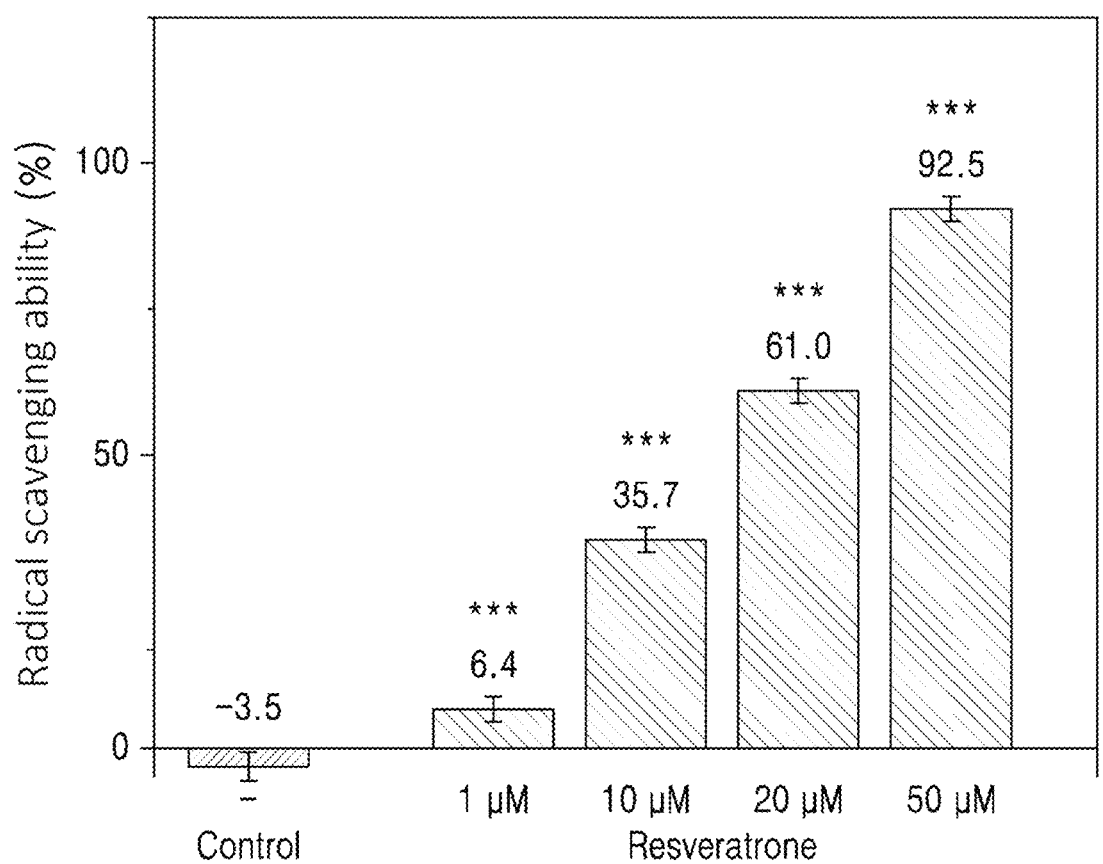
FIG. 2 is a graph showing the result of evaluating the antioxidant efficacy (DPPH assay) of resveratrone compounds according to an example of the present disclosure.

Referring to FIG. 2, the radical scavenging ability was confirmed in test groups treated with resveratrone at a concentration of 1 µM to 50 µM.

Test Example 3: Evaluation of Whitening Efficacy of Resveratrone (Inhibitory Activity of B16F10 Intracellular Melanin Synthesis)

1) B16F10 cells were cultured.
2) The cells were inoculated in an appropriate number, and after 24 hours, all groups except blank were treated with α-MSH and samples, respectively.
3) The cells were cultured for 72 hours in culture media treated with respective samples.
4) The cells were lysed, the supernatant was separated, and the absorbance value of the supernatant was measured.
5) The amount of protein in each supernatant was measured and analyzed by the BCA method.
6) The melanin synthesis value measured in the supernatant was corrected into the amount of protein to calculate the amount of melanin synthesis per unit cell.

Figure 3:
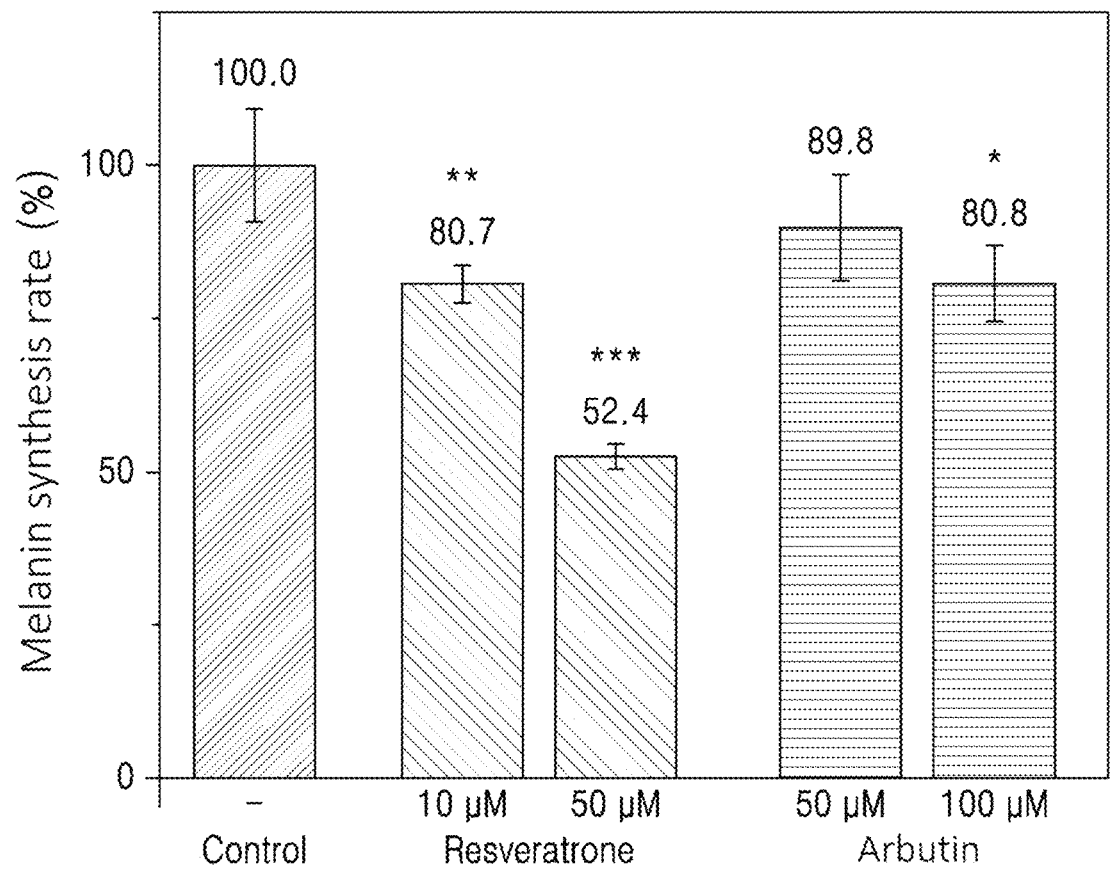
FIG. 3 is a graph showing the result of evaluating the whitening efficacy (inhibitory activity of B16F10 intracellular melanin synthesis) of resveratrone compounds according to an example of the present disclosure.

Referring to FIG. 3, inhibition of melanin synthesis was confirmed in test groups treated with resveratrone at a concentration of 10 µM to 50 µM (Arbutin: positive control).

Test Example 4: Evaluation of Whitening Efficacy of Resveratrone (Inhibitory Ability of B15F10 Extracellular Melanin Synthesis)

1) B16F10 cells were cultured.
2) The cells were inoculated in an appropriate number, and after 24 hours, all groups except blank were treated with α-MSH and samples, respectively.
3) The cells were cultured for 72 hours in culture media treated with respective samples.
4) The absorbance values of the cell culture media were measured.
5) The cells were lysed, the supernatant was separated, and the amount of protein was measured by the BCA method to correct the amount of melanin synthesis.
6) The measured melanin synthesis value was corrected into the amount of protein to calculate the amount of melanin synthesis per unit cell.

Figure 4:
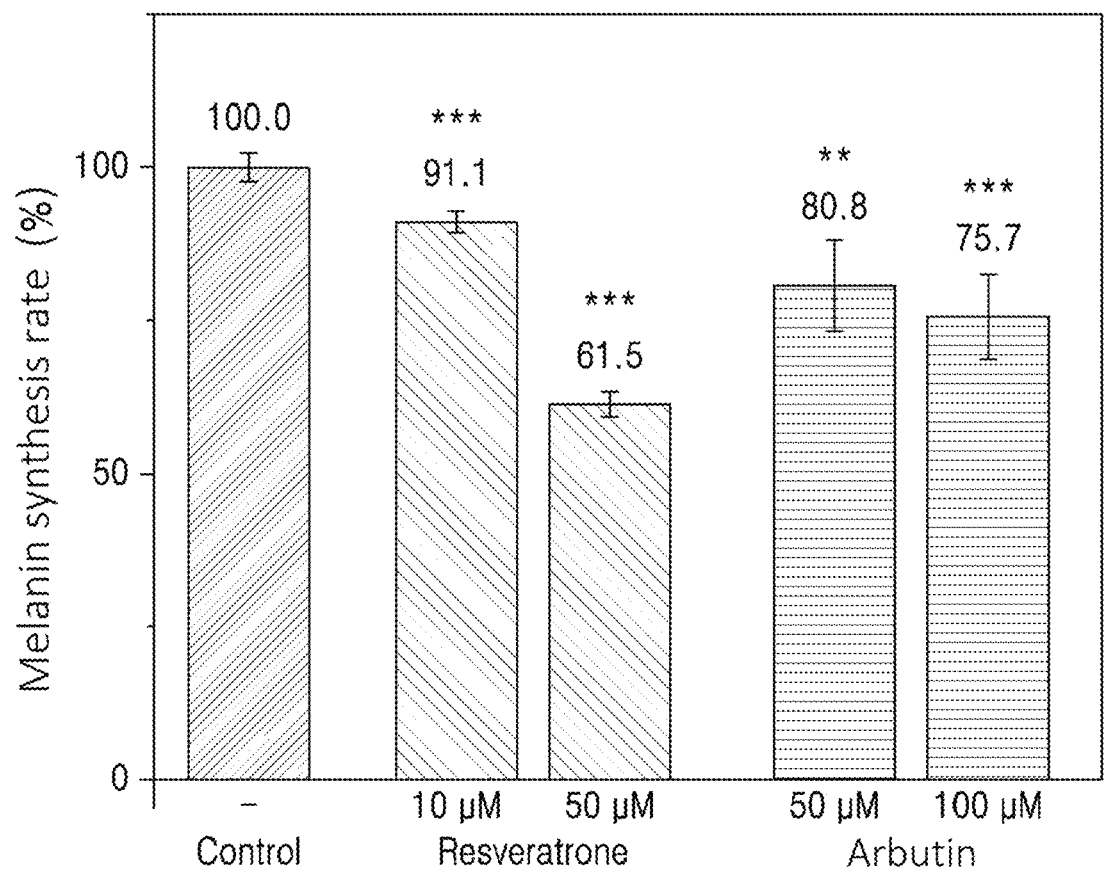
FIG. 4 is a graph showing the result of evaluating the whitening efficacy (inhibitory ability of B15F10 extracellular melanin synthesis) of resveratrone compounds according to an example of the present disclosure.

Referring to FIG. 4, inhibition of melanin synthesis was confirmed in test groups treated with resveratrone at a concentration of 10 µM to 50 µM (Arbutin: positive control).

Test Example 5: Evaluation of Whitening Efficacy of Resveratrone (Inhibitory Ability of Tyrosinase Activity)

1) Human-derived normal pigment cells were inoculated in an appropriate number and cultured for 1 day.
2) The culture medium was replaced with culture media treated with respective samples and cultured for 72 hours.
3) The cells were lysed, the supernatant was separated, and the absorbance value of the supernatant was measured at 475 nm at 30 minute intervals while the supernatant was allowed to react with dopa, a reactant, at 37° C.
4) The amount of protein in the cell lysis supernatant was measured by the BCA method to correct a tyrosinase (melanin synthase) measurement value.

Figure 5:
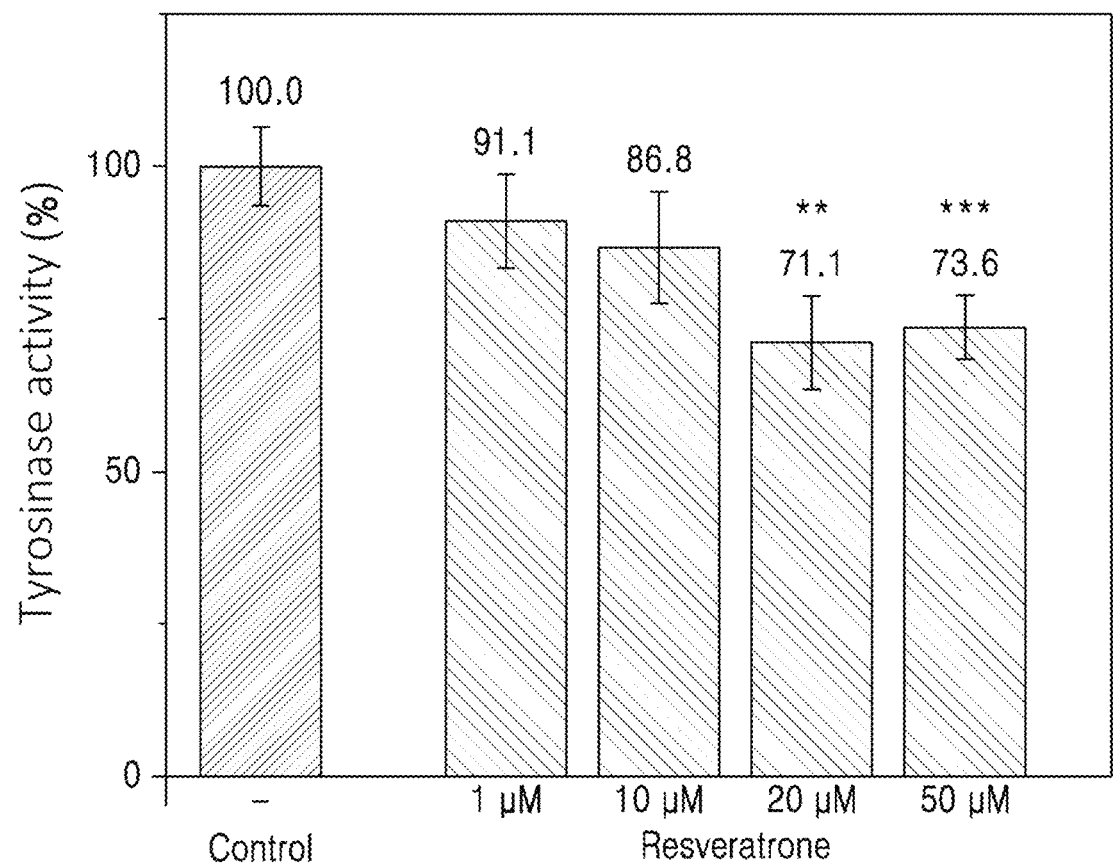
FIG. 5 is a graph showing the result of evaluating the whitening efficacy (inhibitory ability of tyrosinase activity) of resveratrone compounds according to an example of the present disclosure.

Referring to FIG. 5, inhibition of tyrosinase activity was confirmed in test groups treated with resveratrone at a concentration of 1 µM to 50 µM.

Test Example 6: Evaluation of Wrinkle Improvement Efficacy of Resveratrone (Collagen Synthesis Efficacy)

1) Human-derived normal fibroblasts were inoculated at $2 \times 10^5/6$ well and cultured.
2) Culture was performed for 1 day under starvation conditions.
3) The cells were treated with samples at different concentrations, respectively, and cultured for 24 hours.
4) The cells were washed and then irradiated with UV, followed by culture for 48 hours.
5) The amount of collagen expression in the cell culture medium was measured and analyzed.

Figure 6:
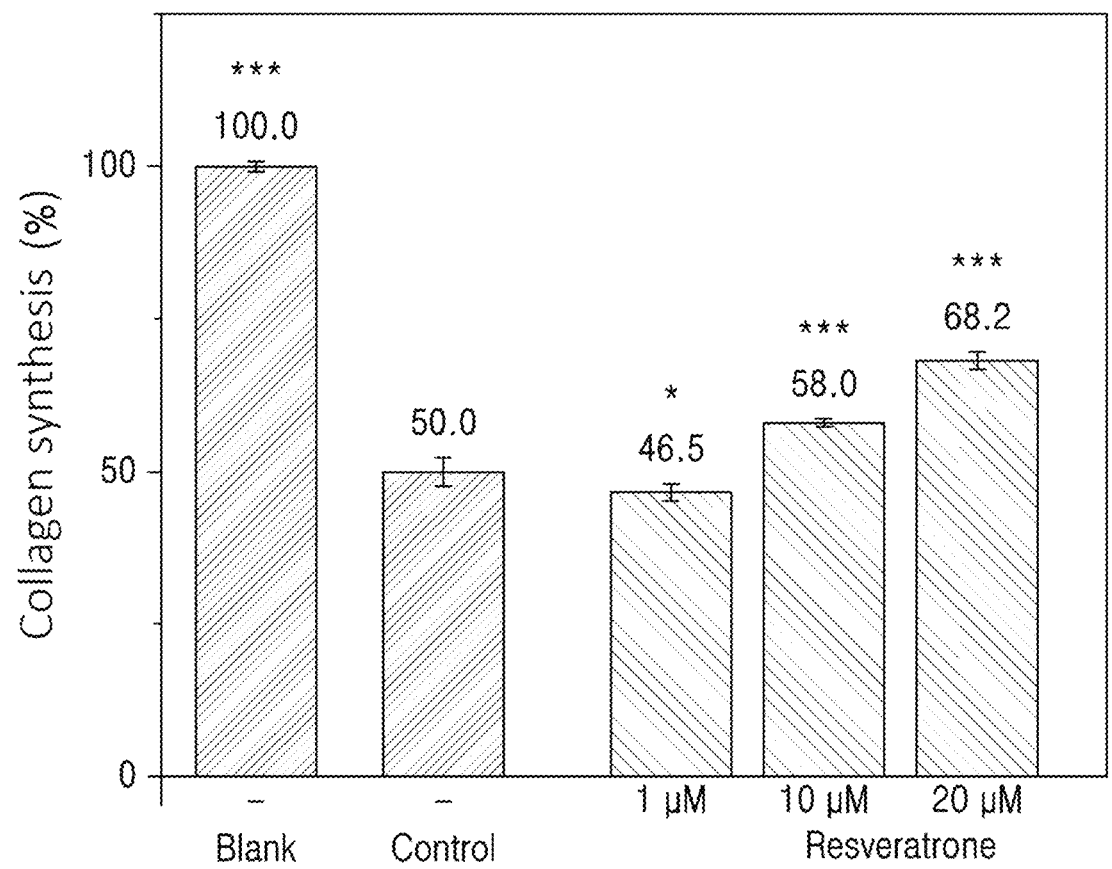
FIG. 6 is a graph showing the result of evaluating the wrinkle improvement efficacy (collagen synthesis efficacy) of resveratrone compounds according to an example of the present disclosure.

Referring to FIG. 6, an increase in collagen synthesis was confirmed in test groups treated with resveratrone at a concentration of 10 μM to 20 μM.

Test Example 7: Evaluation of Anti-Acne Efficacy of Resveratrone (Antibacterial Efficacy of *Propionibacterium Acnes*)

1) *Propionibacterium acnes*, anaerobic acne bacteria, were cultured under anaerobic culture conditions.
2) The strain was prepared by adjusting the turbidity to McFarland standard NO. 1, followed by dilution of 1/20 in a liquid culture medium.
3) Liquid nutrient media were treated with samples at different concentrations, respectively.
4) After 100 μL of each of the liquid nutrient media treated with the samples was dispensed, 10 μL of the prepared strain was inoculated to each medium.
5) After the strain was cultured for 72 hours under anaerobic culture conditions, the number of bacteria was measured and analyzed.

Figure 7:
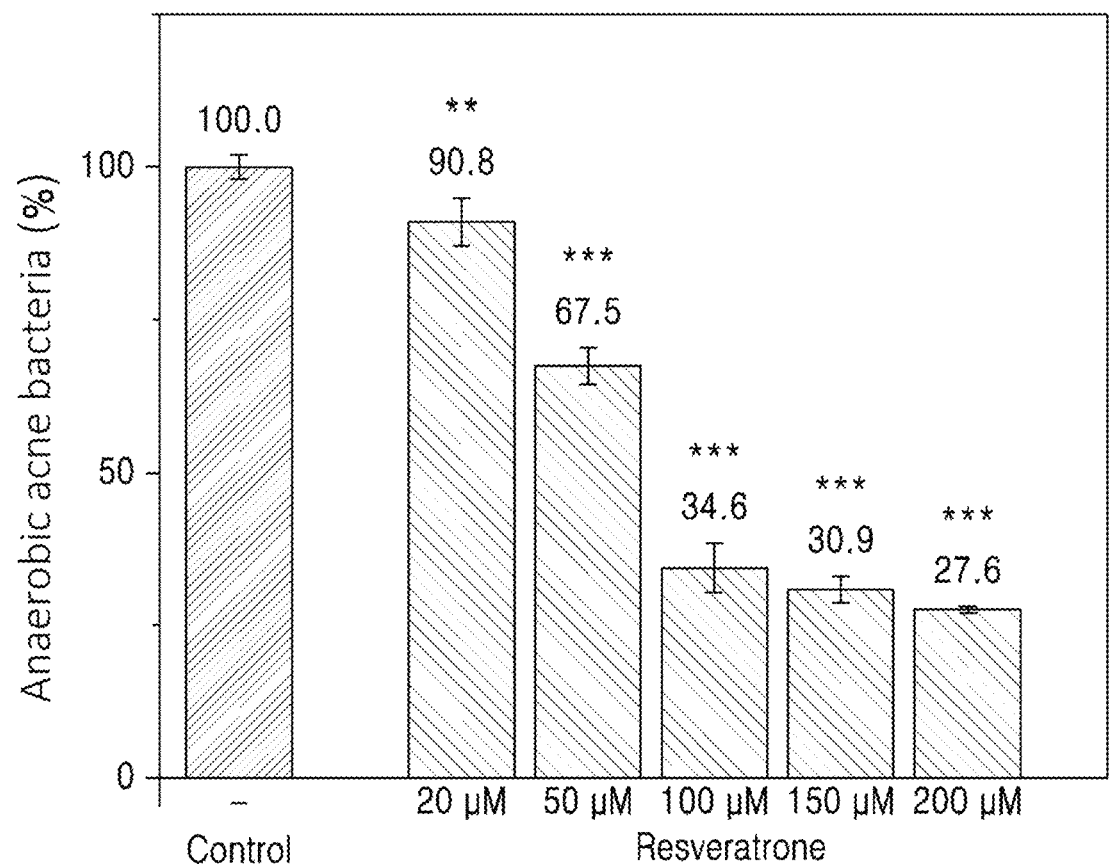
FIG. 7 is a graph showing the result of evaluating the anti-acne efficacy (antibacterial efficacy of *Propionibacterium acnes*) of resveratrone compounds according to an example of the present disclosure.

Referring to FIG. 7, inhibition of bacterial growth was confirmed in test groups treated with resveratrone at a concentration of 20 μM to 200 μM.

Test Example 8: Measurement of Absorbance of Resveratrone

1) Resveratrone was dissolved in an organic solvent at a concentration of 10 μM to 50 μM.
2) The absorbance of resveratrone was measured by using a spectrophotometer.

Figure 8:
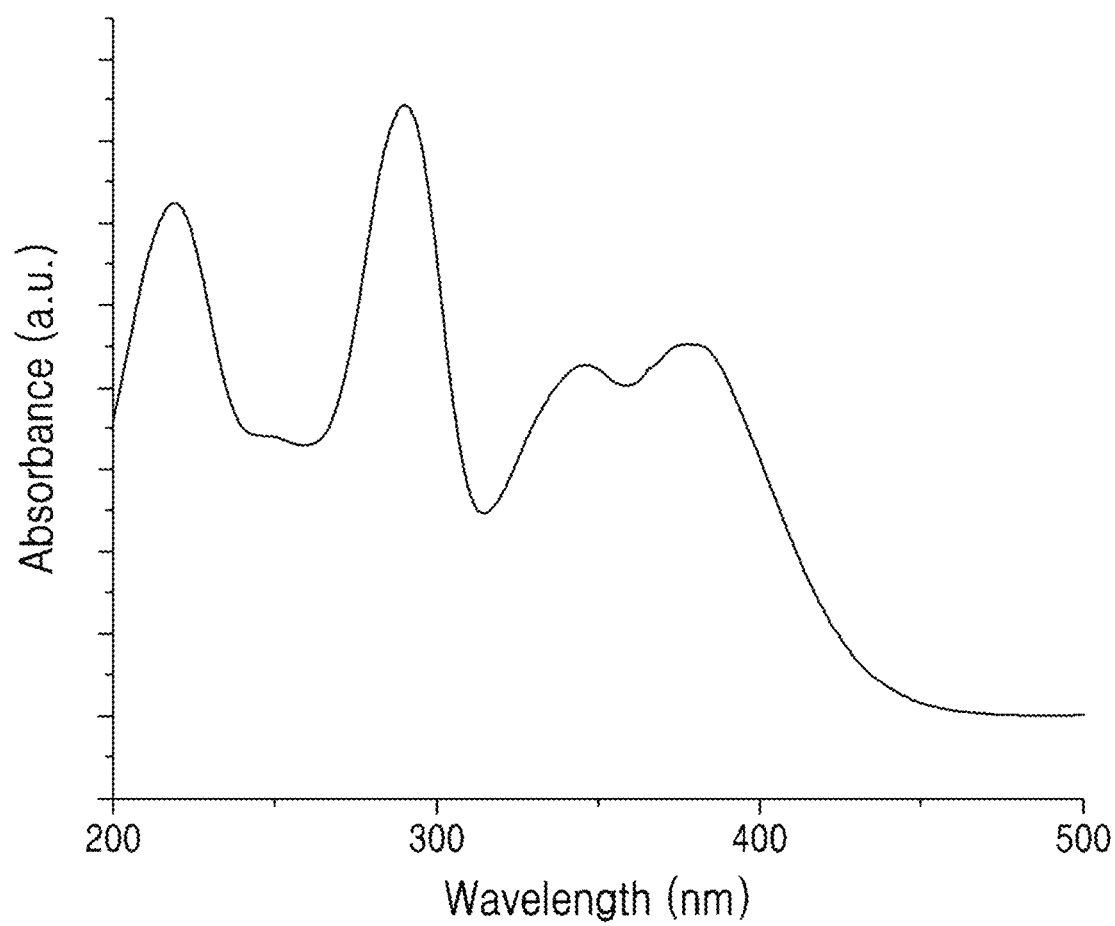
FIG. 8 shows an absorbance spectrum of a resveratrone compound according to an example of the present disclosure.

Referring to FIG. 8, absorption was confirmed in all UV regions of UV-A (320 nm to 400 nm), UV-B (280 nm to 320 nm), and UV-C (200 nm to 280 nm).

Test Example 9: Measurement of Sun Protection Factor of Resveratrone-Containing Cream 1) A resveratrone-containing cream was prepared by mixing purified water (65%), glycerol (7%), olive emulsified wax (5%), jojoba oil (20%), and resveratrone (3%) while heating them at 75° C. or more.
2) After the prepared cream was applied and spread well by 2.0 mg/cm² on the back, a sun protection factor (SPF, UV-B protection factor) and a protection factor of UVA (PFA, UV-A protection factor) were measured according to the measurement method notified by the Ministry of Food and Drug Safety.

Figure 9A:
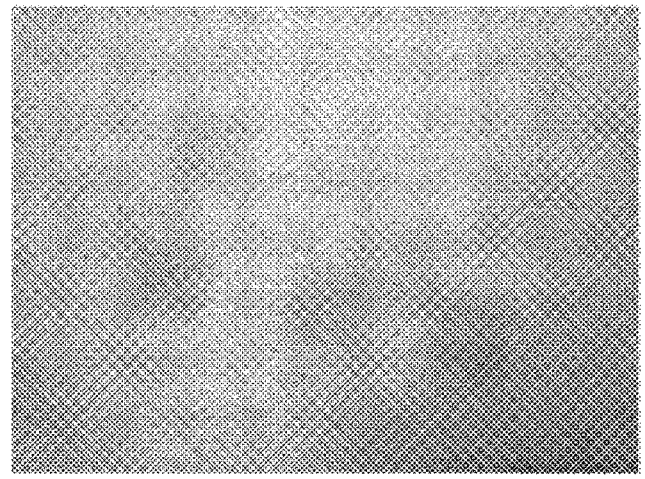
FIGS. 9A and 9B show photos for measuring sun protection factors of a resveratrone compound-containing cream according to an example of the present disclosure.
Figure 9B:
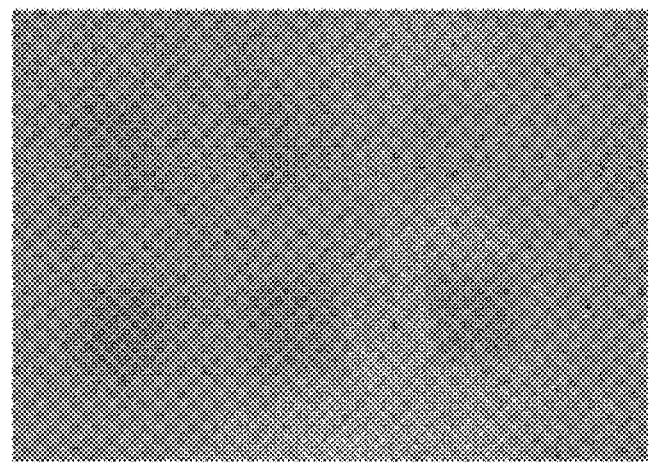

Referring to FIGS. 9A and 9B, a sun protection effect was confirmed by a clinical test result including an expected SPF of 4.0 and an expected PFA of 4.8.

The above description of the example embodiments is provided for the purpose of illustration, and it would be understood by those skilled in the art that various changes and modifications may be made without changing technical conception and essential features of the example embodiments. Thus, it is clear that the above-described example embodiments are illustrative in all aspects and do not limit the present disclosure. For example, each component described to be distributed can be implemented in a combined manner.

The scope of the inventive concept is defined by the following claims and their equivalents rather than by the detailed description of the example embodiments. It shall be understood that all modifications and embodiments conceived from the meaning and scope of the claims and their equivalents are included in the scope of the inventive concept.

What is claimed is:
1. A cosmetic, comprising a cosmetic composition, wherein the cosmetic composition comprising:
  a compound represented by Chemical Formula 1 as an active ingredient, and
  wherein the cosmetic includes one or more functions selected from the group consisting of skin regeneration, skin whitening, skin wrinkle improvement, anti-acne, and antioxidation:

[Chemical Formula 1]

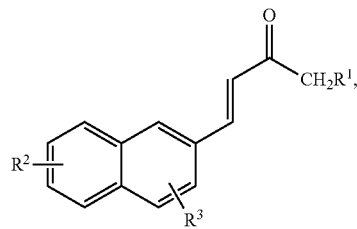

wherein, in Chemical Formula 1,
$R^1$ is hydrogen; a halogen group; a linear or branched $C_{1-6}$ alkyl group; a $C_{3-6}$ cycloalkyl group; a linear or branched $C_{1-6}$ alkoxy group; a $C_{2-6}$ heterocycloalkyl group containing N, O, or S as a hetero atom; or a phenyl group unsubstituted or substituted with one or more substituents selected from the group consisting of a halogen group, amino group, nitrile group, nitro group, a $C_{1-10}$ alkyl group, a $C_{2-10}$ alkenyl group, a $C_{1-10}$ alkoxy group, a $C_{3-6}$ cycloalkyl group, a $C_{2-6}$ heterocycloalkyl group containing N, O, or S as a hetero atom, a $C_{6-16}$ aryl group, and a $C_{5-15}$ heteroaryl group containing N, O, or S as a hetero atom, and
each of $R^2$ and $R^3$ is independently selected from hydroxyl group, a linear or branched $C_{1-6}$ alkoxy group, and a benzoyl group.

2. The cosmetic of claim 1,
wherein the compound represented by Chemical Formula 1 is represented by the following Chemical Formula 2:

[Chemical Formula 2]

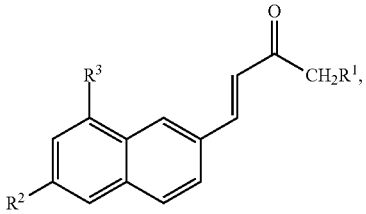

wherein, in Chemical Formula 2,
$R^1$ is hydrogen; a halogen group; a linear or branched $C_{1-6}$ alkyl group; a $C_{3-6}$ cycloalkyl group; a linear or branched $C_{1-6}$ alkoxy group; a $C_{2-6}$ heterocycloalkyl group containing N, O, or S as a hetero atom; or a phenyl group unsubstituted or substituted with one or more substituents selected from the group consisting of a halogen group, amino group, nitrile group, nitro group, a $C_{1-10}$ alkyl group, a $C_{2-10}$ alkenyl group, a $C_{1-10}$ alkoxy group, a $C_{3-6}$ cycloalkyl group, a $C_{2-6}$ heterocycloalkyl group containing N, O, or S as a hetero atom, a $C_{6-16}$ aryl group, and a $C_{5-15}$ heteroaryl group containing N, O, or S as a hetero atom, and each of $R^2$ and $R^3$ is independently selected from the group consisting of hydroxyl group, a linear or branched $C_{1-6}$ alkoxy group, and a benzoyl group.

3. The cosmetic of claim 1, wherein the compound represented by Chemical Formula 1 is selected from the group consisting of

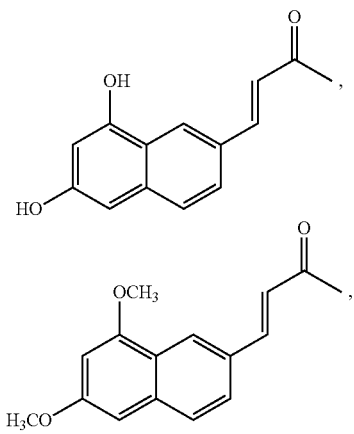

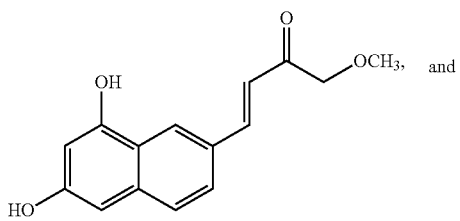

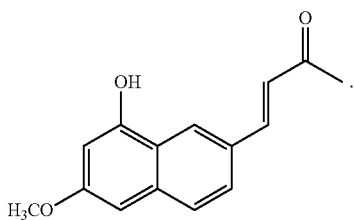

4. The cosmetic of claim 1, wherein a formulation of the cosmetic is selected from the group consisting of toner, essence, lotion, cream, gel, powder, pack, surfactant of soap or shampoo, rinse, oil, foundation, hair dye, and wax.

\* \* \* \* \*